United States Patent [19]
Homma et al.

[11] Patent Number: 5,679,556
[45] Date of Patent: *Oct. 21, 1997

[54] PROCESS FOR THE RECOVERY AND PURIFICATION OF XANTHAN GUM

[75] Inventors: Taira Homma; Kanji Murofushi; Shigehiro Nagura, all of Niigata-ken, Japan

[73] Assignees: Shin-Etsu Chemical Co., Ltd., Tokyo, Japan; Shin-Etsu Bio, Inc., San Diego, Calif.

[*] Notice: The term of this patent shall not extend beyond the expiration date of Pat. No. 5,416,206.

[21] Appl. No.: 484,566

[22] Filed: Jun. 7, 1995

Related U.S. Application Data

[63] Continuation-in-part of Ser. No. 345,076, Nov. 28, 1994, Pat. No. 5,595,892, which is a continuation-in-part of Ser. No. 990,758, Dec. 15, 1992.

[30] Foreign Application Priority Data

Jun. 30, 1994 [JP] Japan .................................. 6-148904
Nov. 29, 1994 [JP] Japan .................................. 6-294172

[51] Int. Cl.$^6$ .............................. C12P 19/06; C12N 1/20
[52] U.S. Cl. ............... 435/104; 424/93.4; 424/282.1; 435/252.1; 435/822; 435/910; 536/114
[58] Field of Search ............................ 424/93.4, 282.1; 435/104, 252.1, 822, 910; 536/114

[56] References Cited

FOREIGN PATENT DOCUMENTS 0549230  6/1993  European Pat. Off. .
0545674  9/1993  European Pat. Off. .

OTHER PUBLICATIONS

Patent Abstracts of Japan, vol. 18, No. 191 (C-1186), Apr. 4, 1994, and JP A 5-345801 of Dec. 27, 1993.

Patent Abstracts of Japan, vol. 98 (C-339) [2155] Apr. 15, 1986, and JP A 60-227692 of Dec. 12, 1985.

*Primary Examiner*—David M. Naff
*Assistant Examiner*—Deborah K. Ware
*Attorney, Agent, or Firm*—McAulay Fisher; Nissen Goldberg & Kiel, LLP

[57] ABSTRACT

A xanthan gum-containing fermented solution is subjected to an enzyme treatment for solubilizing the microbial cells present in the fermented solution. While the fermented solution having undergone the enzyme treatment is maintained at a temperature of 50° C. to 80° C., and xanthan gum is precipitated by adding an hydrophilic organic solvent incapable of dissolving xanthan gum to the fermented solution. When a rotary turbine is used, the precipitate can be cut with a shearing cutter to recover a finely-divided fibrous product.

14 Claims, 1 Drawing Sheet

FIG.1

PROCESS FOR THE RECOVERY AND PURIFICATION OF XANTHAN GUM

CROSS-REFERENCE TO RELATED APPLICATIONS

This application is a continuation-in-part of application Ser. No. 08/345,076 filed Nov. 28, 1994, now U.S. Pat. No. 5,595,892 which in turn, is a continuation-in-part of application Ser. No. 07/990,758, filed Dec. 15, 1992, the contents of each of which are incorporated by reference.

FIELD OF THE INVENTION

This invention relates to a process for the recovery and purification of xanthan gum.

RELATED ART STATEMENT

Generally, water-soluble viscous polysaccharides including gum arabic, xanthan gum, guar gum, ramsan gum and the like are widely used in various fields of industry, such as, food, paints, papermaking, cosmetics, medicines and oil recovery, and the demand for them is increasing in recent years. Among others, xanthan gum exhibits excellent thickening and emulsion-stabilizing effects and other properties, such as, salt resistance, pH resistance and stability to enzymes, and its range of industrial application as a useful additive is extending.

Conventionally, xanthan gum is obtained by aerobically cultivating a bacterium of the genus Xanthomonas (e.g., *X. campestris*) in a culture medium containing a carbon source such as glucose, molasses or starch, a water-soluble nitrogen source, such as, peptone or yeast extract, and a magnesium salt, phosphate ion and other minor components. After cultivation, the broth or solution containing the dissolved xanthan gum is treated to kill the bacterium therein. The xanthan gum is then recovered from the broth by precipitation. This is carried out by adding a non-solvent for the xanthan gum, i.e., a liquid in which the xanthan gum is insoluble, to the broth in amount to cause the xanthan gum to precipitate. Such non-solvents are generally organic liquids, such as, alcohols, with isopropanol and ethanol being preferred, although other non-solvents may be used. The thus obtained precipitate is then dried.

One problem with the precipitation step is the fact that relatively large volumes of the non-solvent can be required in an effort to maximize the recovery of xanthan gum. The non-solvent is a relatively costly component in the process and for this reason alone, it is highly desirable to minimize the amount used. In addition, as the amount of non-solvent increases, larger size vessels and equipment are required which also increases the costs. Another problem is that the non-solvent is usually a material which is environmentally disadvantageous and must be recovered so as not to cause an adverse environmental impact as well as make it available for reuse in the process so as to further reduce costs. Of course, such recovery steps themselves add to the cost and complexity of the process. Consequently, to the extent that the amount of the non-solvent required to obtain satisfactory recovered amounts of xanthan gum product can be reduced, favorable impact on all aspects of the process economics can be achieved.

Various processes for the production of xanthan gum are disclosed in U.S. Pat. Nos. 3,020,206, 3,251,479, 3,391,060, 3,433,708, 3,594,280, 4,282,321 and 3,659,026.

Alternatively, xanthan gum can also be produced by using, in place of *Xanthomonas campestris*, other Xanthomonas bacteria known to be productive microorganisms, such as, *X. carorate*, *X. incanae*, *X. begoniae*, *X. papavericola*, *X. translucens*, *X. vasculorum* and *X. hederae*.

In the purification of xanthan gum, it is generally known that centrifugation or cake filtration may be used to remove any undissolved matter (such as microbial cell residue and water-insoluble unconsumed nitrogenous component) present in a fermented solution. However, since fermented solutions are highly viscous, these techniques require a water dilution step and a subsequent concentration step and are hence impractical from the viewpoint of cost and operation.

In contrast, a purification method which comprises treating a fermented solution with an enzyme or enzymes for the purpose of disintegrating and solubilizing the microbial cell residue or removing the microgel is also known and many processes have been proposed.

For example, as enzyme treatment processes for disintegrating and solubilizing the microbial cell residue, there have been proposed a process using an acid protease and a neutral protease (U.S. Pat. Nos. 3,966,618 and 4,010,071); a process in which, after treatment with a protease, the resulting aqueous polymer solution is brought into contact with a siliceous solid to remove the microbial cell residue therefrom (U.S. Pat. No. 4,119,491); a process using a compound enzyme having b-1,3-glucanase activity and protease activity (European Patent No. 39,962); a process using an enzyme having nuclease activity (U.S. Pat. No. 4,729,958); a process in which a fermented solution is clarified by causing an alkaline protease and lysozyme to act thereon successively (European Patent 0,549,230); and the like. As enzyme treatment processes for removing the microgel, there have been proposed an enzyme treatment process using a polysaccharase and a protease (U.S. Pat. No. 4,431,734); a process involving the combined use of an enzyme having polygalacturonase activity and an enzyme having protease activity (U.S. Pat. No. 4,904,586); a purification process using cellulase (U.S. Pat. No. 4,416,990); and the like. As compared with conventional purification techniques such as filtration and centrifugation, all of these enzyme treatment processes eliminate the necessity of troublesome steps such as dilution and concentration, and are hence advantageous purification processes from economic and operational points of view. On the other hand, a process for the recovery of xanthan gum wherein a trivalent ion, an aliphatic alkylamine, an aluminum salt or the like is used in combination with an organic solvent to precipitate and recover xanthan gum is proposed in Japanese Patent Laid-Open Nos. 196,099/'84, 53,502/'84 and 53,503/'84 as well as U.S. patent application Ser. No. 710,812. It is stated therein that the amount of organic solvent used can be reduced or the viscosity of the xanthan gum-containing fermented solution can be reduced to obtain an easy-to-handle fermented solution. However, it is feared that the salt added may not be completely removed during recovery and remain in the xanthan gum as an impurity. In Japanese Patent Laid-Open No. 156,594/'80, there is proposed a process for the recovery of xanthan gum wherein, in order to obtain xanthan gum capable of exhibiting high viscosity, the temperature of a xanthan gum-containing fermented solution is adjusted to 70°–90° F. (7°–18° C.) and xanthan gum is precipitated and recovered therefrom with the aid of an organic solvent such as isopropanol. However, there is no mention of the purifying effect which might be produced during recovery. In U.S. Pat. No. 3,591,578, it is described that xanthan gum having excellent acid resistance and salt resistance can be obtained by heat-treating a xanthan gum-containing fermented solution at a temperature of 80°–130° C. and a pH of 6.3–6.9 for 10–120 minutes, cooling the fermented solution to room temperature, and recovering xanthan gum with the aid of an organic solvent such as isopropanol. However, the temperature conditions in the recovery step are not considered and no mention of the purifying effect is found therein.

In Japanese Patent Laid-Open No. 5,301/'83, there is proposed a process in which, after a xanthan gum-containing fermented solution is heated at a temperature of 100° C. or above, a divalent ion is added thereto and xanthan gum is precipitated and recovered with the aid of an organic solvent. It is stated therein that the amount of organic solvent used can be reduced. However, it is feared that the temperature of 100° C. or above may exert an adverse influence on the viscosity properties of the xanthan gum. Moreover, it is presumed that the divalent ion added may not be completely removed during recovery and may remain in the xanthan gum, exerting an adverse influence on the properties of the resulting product.

In Japanese Patent Laid-Open No. 72,697/'81, there is proposed a process which comprises adding isopropanol to a xanthan gum-containing fermented solution in an amount insufficient to precipitate xanthan gum, heat-treating the fermented solution at a temperature of 100° C. or above, removing solid matter from the fermented solution by cake filtration, and adding more isopropanol to the remaining fermented solution so as to precipitate and recover xanthan gum. It is stated therein that the ability of xanthan gum to exhibit high viscosity and the purifying effect can be improved. However, this process cannot be regarded as preferable because the cake filtration employed in this case requires troublesome operation and the disposal of spent cake poses an additional problem. Moreover, it is feared that, since the fermented solution is treated at a temperature of 100° C. or above, the viscosity properties of xanthan gum may be affected adversely.

Thus, none of the conventional recovery processes involve well-defined conditions for the preparation of purified xanthan gum in combination with a purification technique based on an enzyme treatment. That is, there is no well-established method for recovering fully purified xanthan gum from a xanthan gum-containing fermented solution in which any undissolved matter derived from microorganisms has been solubilized by an enzyme treatment having a bacteriolytic effect.

In addition, relatively large mount of non-solvent are required to maximize the precipitation of the xanthan gum and it is desired to reduce the mounts of such materials which not effecting the efficiency and effectiveness of the mount of product obtained.

SUMMARY OF THE INVENTION

Accordingly, it is an object of the present invention to provide a process for the recovery and purification of xanthan gum which enables fully purified xanthan gum to be obtained from a xanthan gum-containing fermented solution.

It is another object of the present invention to provide a process for obtaining such fully purified xanthan gum using an enzyme treatment for solubilizing the microbial cells present therein.

It is another object of the invention to provide a method for precipitating xanthan gum from an aqueous solution thereof using reduced mounts of an organic non-solvent to precipitate the xanthan gum compared to the mount conventionally required. In particular, the inventive process utilizes about 20% less of the non-solvent as compared to the mount used in the conventional process.

Moreover, the inventive process provides a highly purified xanthan gum having good transparency without detracting from its inherent viscosity. The recovered xanthan gum exhibits reduced contents of impurities, such as, nitrogenous components, yellow-colored components and metallic salts. As used herein, the term yellow colored components refers to impurities which tend to impart a yellow or off white color to the xanthan gum product.

The above objects are achieved by the steps of subjecting a xanthan gum-containing broth to an enzyme treatment to solubilize the microbial cells present in the fermented solution, maintaining the thus treated fermented solution at a temperature of 50° to 80° C., for a time period sufficient to achieve the desired degree of purification of the broth and xanthan gum therein, and then precipitating the dissolved xanthan gum by adding an hydrophilic organic liquid which is a non-solvent for xanthan gum, i.e., is incapable of dissolving xanthan gum, or is a poor solvent therefore.

BRIEF DESCRIPTION OF THE DRAWING

The present invention will become more fully understood from the detailed description given hereinbelow and the accompanying drawing which is given by way of illustration only, and thus is not limitative of the present invention.

DETAILED DESCRIPTION OF THE PREFERRED EMBODIMENTS

In one embodiment of the present invention, the hydrophilic organic solvent incapable of dissolving xanthan gum is isopropanol or an aqueous solution of isopropanol having an isopropanol concentration of not less than 80% by weight.

In another embodiment of the present invention, the weight ratio of the enzyme treated fermented broth or solution to the hydrophilic organic solvent incapable of dissolving xanthan gum ranges from 1:1.0 to 1:1.5.

In still another embodiment of the present invention, the enzyme treatment step for solubilizing the microbial cells present in the fermented broth or solution comprises the steps of adjusting the pH of the solution to an initial value in the range from 9 to 12.5, if necessary. Thus, if the pH of the broth or solution is within this range after termination of the fermentation, it is not necessary to further adjust the pH value. The broth or solution within this pH range is then heated at a temperature of 45° to 70° C., preferably 50° to 60° C., for 30 minutes or more. Immediately after this heat-treating step, an alkaline protease is added to the fermented solution in an mount of 10 to 500 ppm and the thus obtained mixture is heated at a temperature of 40° to 65° C., preferably 50° to 60° C., and a pH of 6 to 10 for 30 minutes or more. Thereafter, lysozyme, in an mount of 0.5 to 100 ppm is added to the thus treated solution and this mixture is heated at a temperature of 25° to 60° C., preferably 50° to 60° C., and a pH of 5.5 to 8.0 for 30 minutes or more.

In a further embodiment of the present invention, the enzyme treatment step for solubilizing the microbial cells present in the fermented solution comprises the steps of heat-treating the xanthan gum-containing fermented solution at an initial pH of 9 to 12.5 and a temperature of 45° to 70° C., preferably 50° to 60° C., for 30 minutes or more; immediately after the heat-treating step, adding lysozyme to the fermented solution in an mount of 0.5 to 100 ppm and carrying out a lysozyme treatment at a temperature of 25° to 60° C., preferably 50° to 60° C., and a pH of 5.5 to 8.0 for 30 minutes or more; and then adding an alkaline protease to the fermented solution in an mount of 10 to 500 ppm and carrying out an alkaline protease treatment at a temperature of 40° to 65° C., preferably 50° to 60° C., and a pH of 6 to 10 for 30 minutes or more.

In a still further embodiment of the present invention, the process for the recovery and purification of xanthan gum further comprises the steps of mixing the xanthan gum-containing fermented solution having undergone the enzyme treatment with the hydrophilic organic solvent incapable of dissolving xanthan gum and feeding the mixture to a cutting device to cut the precipitate formed in the resulting mixture into a finely-divided fibrous product, and separating and recovering the suspended finely-divided fibrous product from the mixture.

Generally, the mount of the non-solvent can be about 20% by weight less than that required in the conventional process to precipitate the product.

We have further discovered that with the inventive process, the amount of non-solvent required to precipitate the xanthan gum product from the broth is less than that conventionally required to recover the same or and equivalent amount of xanthan gum. This provides substantial advantages with respect to costs and environmental impact of the process. Nonetheless, the xanthan gum product obtained exhibits good transparency and viscosity properties in aqueous solution as well as decrease impurity content, e.g., nitrogenous components, yellowing components and metallic salts. In addition, these advantages are obtained using a relatively simple process and apparatus. In one embodiment, the xanthan gum-containing solution after treatment with the enzyme, is fed to a rotary turbine while being maintained at the prescribed temperature and mixed with the organic solvent to precipitate xanthan gum in the form of a finely-divided fibrous product. This leads to an extension of the range of its use for industrial purposes.

In the practice of the present invention, the xanthan gum-containing fermented solution, after the enzyme treatment, is maintained at a temperature of 50° to 80° C. As used herein, the expression "maintaining the fermented solution at a temperature of 50° to 80° C." also includes the heating the fermented solution to a temperature within this range. At temperatures higher than 80° C., no appreciable improvement in purifying effect is achieved, but rather the viscosity properties of the recovered xanthan gum may be affected adversely. At temperatures lower than 50° C., impurities such as nitrogenous components, yellowing components and metallic salts derived from the culture medium components or the microorganism cannot be thoroughly removed and a significant amount of such impurities may remain in the xanthan gum.

The preferred non-solvent used in the present invention is isopropanol or an aqueous solution of isopropanol having an isopropanol concentration of not less than 80% by weight. Other organic solvents, such as, acetone and ethanol are not desirable because the mount of the organic solvent used is greater than that required with isopropanol and results in difficulties in operation and increased costs. If the aqueous solution of isopropanol has an isopropanol concentration of less than 80% by weight, the xanthan gum shows an increase in water content and may hence become difficult to precipitate.

No particular limitation is placed on the temperature of the organic non-solvent used in the present invention.

In the practice of the present invention, the weight ratio of the fermented solution to the organic solvent should range from 1:1.0 to 1:1.5. If the proportion of the organic solvent is greater than 1.5, no appreciable improvement in the purifying effect is achieved in spite of the increase in the amount of organic solvent used. If the proportion of the organic solvent is less than 1.0, xanthan gum is not fully precipitated.

The enzyme treatment of the present invention is carried out after the xanthan gum-containing fermented solution is heated at an initial pH of 9 to 12.5, preferably 10 to 12, and a temperature of 45° to 70° C., preferably 50° to 60° C., for 30 minutes or more. Without this pretreatment, the effects of the enzyme treatment may not be produced or a long time may be required to produce the effects.

The enzyme treatment is carried out in two stages using an alkaline protease and lysozyme. The treatment with an alkaline protease is carried out at a pH of 6 to 10, preferably 7.5 to 9.0, a concentration of 10 to 500 ppm, and a temperature of 40° to 65° C., preferably 50° to 60° C., for 30 minutes or more. If the pH is lower than 6, the activity of the alkaline protease may be reduced, while if the pH is higher than 10, the properties of the product may be deteriorated. If the concentration is lower than 10 ppm, the alkaline protease fails to exhibit its effect satisfactorily, while if the concentration is higher than 500 ppm, no appreciable improvement in bacteriolytic effect is achieved in spite of the increase in the amount of enzyme used and it is undesirable from the viewpoint of cost. If the temperature is lower than 40° C., the alkaline protease fails to exhibit its effect satisfactorily, while if temperature is higher than 65° C., the activity of the alkaline protease may be reduced. If the treating time is less than 30 minutes, the alkaline protease fails to exhibit its effect satisfactorily. The treatment with lysozyme is carried out at a pH of 5.5 to 8.0, preferably 6.5 to 7.5, a concentration of 0.5 to 100 ppm, and a temperature of 25° to 60° C., preferably 50° to 60° C., for 30 minutes or more. If the pH is lower than 5.5 or higher than 8.0, the activity of lysozyme may be reduced. If the concentration is lower than 0.5 ppm, lysozyme fails to exhibit its effect satisfactorily, while if the concentration is higher than 100 ppm, no appreciable improvement in bacteriolytic effect is achieved in spite of the increase in the mount of lysozyme used and it is undesirable from the viewpoint of cost. If the temperature is lower than 25° C., lysozyme fails to exhibit its effect satisfactorily, while if temperature is higher than 60° C., the activity of lysozyme may be reduced. If the treating time is less than 30 minutes, lysozyme fails to exhibit its effect satisfactorily. The above-described two enzyme treatments may be carried out in any desired order.

The precipitation of xanthan gum in the present invention is preferably carried out by feeding the organic non-solvent and the xanthan gum-containing fermented solution to an appropriate cutting device so that they may be mixed and the concomitantly formed precipitate xanthan gum is cut into a finely divided form. This avoids the resulting precipitate being in the form of a mass and enhances the removal of impurities.

Figure 1:
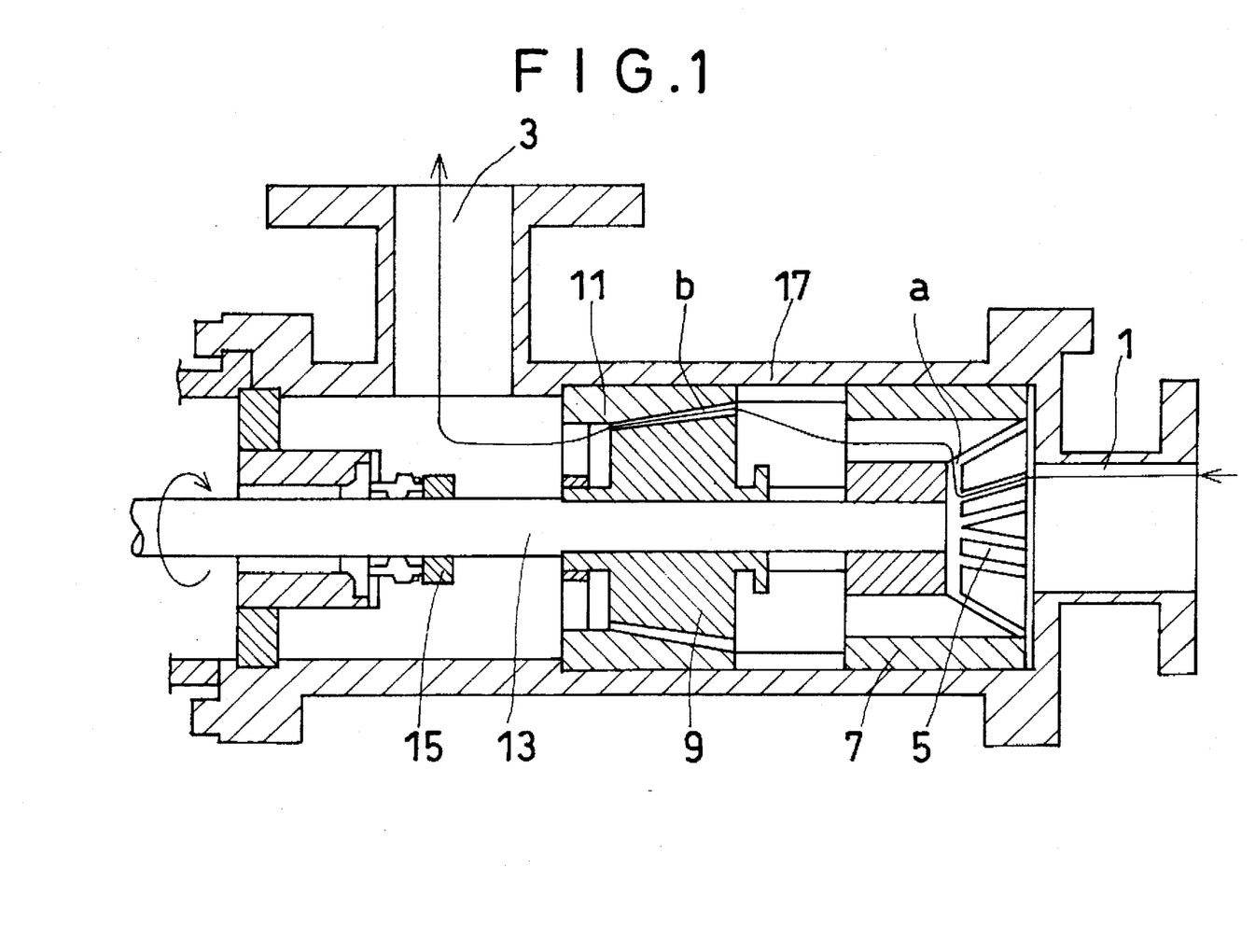
The drawing is a sectional view illustrating one embodiment of the mixing apparatus used for carrying out the present invention.

Referring to the drawing, the mixing apparatus illustrated comprises a driving section, a mixing section and a cutting section. The driving section comprises a motor (not shown), which is disposed outside a cylindrical casing 17, connected with a turbine shaft 13, and isolated from the interior of cylindrical casing 17 by means of a mechanical seal 15. The mixing section and the cutting section are disposed within cylindrical casing 17. Cylindrical casing 17 has an inlet port 1 and an outlet port 3, and turbine shaft 13 is located in the center thereof. The mixing section is composed of a rotary turbine 5 attached to turbine shaft 13 in the vicinity of inlet port 1, and a stator 7 disposed in a position corresponding to rotary turbine 5. The cutting section comprises a shearing cutter made up of a rotary, cutter 9 disposed between the mixing section and outlet port 3, and a stationary cutter 11 surrounding rotary cutter 9 in proximity thereto. Rotary turbine 5 and rotary cutter 9 are configured so as to have a spiral shape inclined toward the axis of turbine shaft 13 and thereby produce conveying power as a result of the rotation of turbine shaft 13.

A gap a is provided between rotary turbine 5 and stator 7, and a gap b is provided between rotary cutter 9 and stationary cutter 11. These gaps may have a size of 0.1 to 5 mm and preferably about 1 mm. If the size of the gaps is greater than 5 mm, the two types of liquids are not fully mixed, resulting in the insufficient precipitation of xanthan gum. Moreover, the precipitated xanthan gum is not cut finely enough in the cutting section.

Within the mixing apparatus, flow paths are formed through the various parts and the gaps between parts. As a result, liquid is conveyed from inlet port 1 to outlet port 3, for example, through a flow path indicated by a line with an arrowhead.

When the motor constituting the driving section of the mixing apparatus is operated, turbine shaft 13 is rotated in the direction of the arrow, resulting in the rotation of rotary turbine 5 and rotary cutter 9. The rotational speed may be 1,000 or more revolutions per minutes. If an organic solvent and a xanthan gum-containing fermented solution are fed to inlet port 1 concurrently, these two types of liquids are intermixed by rotary turbine 5. Since the mixture is compressed in gap a, it is further mixed to cause the precipitation of xanthan gum. The fibrous xanthan gum so precipitated, which is delivered from gap a together with the liquid component, passes through the flow paths and enters the gap b of the cutting section where it is finely cut by the shearing cutter made up of rotary cutter 9 and stationary cutter 11. The finely divided xanthan gum obtained in gap b is mixed with the liquid component and discharged from outlet port 3 in the form of a suspension. Since the mixing apparatus has sucking and delivering power, the resulting mixture and the precipitated xanthan gum are continuously conveyed from inlet port 1 to outlet port 3 without staying in the mixing apparatus.

The feed rate of the xanthan gum-containing fermented solution to the mixing apparatus of FIG. 1 is preferably in the range of 1,000 to 1,200 liters per hour, and the feed rate of isopropanol is preferably in the range of 1,200 to 1,900 liters per hour.

If the feed rate of the xanthan gum-containing fermented solution is less than 1,000 liters per hour or the feed rate of isopropanol is greater than 1,900 liters per hour, the precipitate tends to take the form of strings and not thin fibers, and may twine round rotary turbine 5.

If the feed rate of the xanthan gum-containing fermented solution is greater than 1,200 liters per hour or the feed rate of isopropanol is less than 1,200 liters per hour, xanthan gum may not be precipitated satisfactorily.

Using the mixing apparatus of FIG. 1, the following testing examples and comparative examples were carried out. It is to be understood that these testing examples and comparative examples are given for the purpose of demonstrating the effects of the present invention more clearly, and the present invention is by no means limited to these testing examples and comparative examples.

TESTING EXAMPLE 1 a) Composition of a culture medium for preliminary cultivation (1)

| Glucose | 5 g/L |
|---|---|
| Polypeptone | 5.2 g/L |
| Yeast extract | 2.6 g/L |
| NaCl | 9 g/L |
| Water | 3 L | b) Composition of a culture medium for preliminary cultivation (2)

| Glucose | 5 g/L |
|---|---|
| Polypeptone | 5.2 g/L |
| Yeast extract | 2.6 g/L |
| NaCl | 9 g/L |
| Water | 127 L | c) Composition of a culture medium for main cultivation

| Glucose | 50 g/L |
|---|---|
| Polypeptone | 2 g/L |
| $KH_2PO_4$ | 2 g/L |
| $MgSO_4 \cdot 7H_2O$ | 0.5 g/L |
| Minor components | 0.05 g/L |
| Water | 1.170 L |

Two milliliters of a stock culture ($10^°$ cells/mL) of *Xanthomonas campestris* (ATCC 55298) (which was also used in the following testing examples and comparative examples) was inoculated into a 5-liter fermenter containing a culture medium having the above-described composition (a), and subjected to first-stage preliminary cultivation under aerated conditions at pH 6.5–8.5 and 30° C. for 24 hours. Then, this culture solution was inoculated into a 200-liter fermenter containing a culture medium having the above-described composition (b), and subjected to second-stage preliminary cultivation under the same conditions as employed for the first-stage preliminary cultivation. Thereafter, this culture solution was inoculated into a 2,000-liter fermenter containing a culture medium having the above-described composition (c), and subjected to aerated fermentation at pH 6.5–7.0 and 30° C. for 48 hours. Thus, there was obtained a fermented solution or broth containing xanthan gum. Subsequently, this fermented solution was subjected to a two-stage enzyme treatment with an alkaline protease and lysozyme in the 2,000-liter fermenter.

Specifically, while this fermented solution was being stirred, its initial pH was adjusted to 11 by the addition of a 20% aqueous solution of sodium hydroxide, followed by heat treatment at 55° C. for 90 minutes. Thereafter, while the fermented solution was maintained at 55° C., its pH was adjusted to 8.5 by the addition of a 10% aqueous solution of sulfuric acid. On the other hand, an aqueous suspension containing an alkaline protease (Bioprase; manufactured by Nagase Biochemical Co., Ltd.) in an amount of 300 ppm based on the fermented solution was filtered through a 0.4μm microfilter to remove the adsorbent. The resulting filtrate was added to the above pH-adjusted fermented solution and an alkaline protease treatment was carried out with stirring for 2 hours.

Next, while the fermented solution was maintained at 55° C., its pH was adjusted to 6.5 by the addition of a 10% aqueous solution of sulfuric acid. Then, lysozyme (Lysozyme Taiyo; manufactured by Taiyo Chemical Co., Ltd.) was added thereto in an amount of 3 ppm and a lysozyme treatment was carried out with stirring for an hour.

After completion of the enzyme treatment, the fermented solution maintained at 55° C. was fed to a mixing apparatus as illustrated in FIG. 1. An 86 wt. % aqueous solution of isopropanol at 20° C. was added thereto in an amount equal to 1.1 times the weight of the fermented solution and mixed therewith to precipitate xanthan gum in the form of a finely-divided fibrous product, and its state of precipitation was evaluated. Then, the precipitated xanthan gum was recovered and dried in a stream of air. The resulting xanthan gum was analyzed for residual nitrogen content and ash content. Moreover, a 1 wt. % aqueous solution of the dried xanthan gum was prepared and its viscosity, light transmittance and yellowness index were measured.

The results thus obtained are shown in Table 1. The analytical methods employed are as follows.

State of precipitation: This was evaluated on the basis of visual observation and tactile sensation.

Good: The precipitate was a fibrous deposit, the fibers having a uniform length of 3 to 10 cm and was not sticky to the touch;

Fair: The precipitate was a fibrous deposit, the fibers having a un-uniform length. The inside of the precipitate was in a gel state. Its surface it was not sticky to the touch, but in its inside it was a little sticky;

Poor: The precipitate was in a gel state and was in an unseparated or partially separated lump. It was sticky to the touch.

Nitrogen content: 0.65 g of xanthan gum was weighed out and its nitrogen content was determined according to the Kjeldahl method.

Ash content: 3 g of xanthan gum was weighed out, placed in a porcelain crucible, and incinerated by ignition at 500°–550° C. Its ash content was determined by weighing the resulting ash.

Viscosity: This was measured with a Brookfield viscometer (30 rpm) at 20° C. using a No. 3 rotor.

Light transmittance: Using a quartz cell having an optical path length of 2 cm, the percent transmission of visual light having a wavelength of 500 mm was measured using an instrument provided by Kotakishoji Co. Ltd.

Yellowness index: This was measured with an SM Color Computer (manufactured by Suga Test Instruments Co., Ltd.).

TESTING EXAMPLE 2

A xanthan gum-containing fermented solution prepared in the same manner as in Testing Example 1 was subjected to the same enzyme treatment as in Testing Example 1.

After completion of the enzyme treatment, the fermented solution was adjusted to 60° C. While the fermented solution is maintained at 60° C., an 86 wt. % aqueous solution of isopropanol at 45° C. was added thereto in an amount equal to 1.1 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

TESTING EXAMPLE 3

A xanthan gum-containing fermented solution prepared in the same manner as in Testing Example 1 was subjected to the same enzyme treatment as in Testing Example 1.

After completion of the enzyme treatment, the fermented solution was adjusted to 60° C. While the fermented solution was maintained at 60° C., a 99 wt. % aqueous solution of isopropanol at 20° C. was added thereto in an amount equal to 1.3 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1. The results thus obtained are shown in Table 1.

The analytical methods employed are as described in Testing Example 1.

TESTING EXAMPLE 4

A xanthan gum-containing fermented solution prepared in the same manner as in Testing Example 1 was subjected to the same enzyme treatment as in Testing Example 1.

After completion of the enzyme treatment, the fermented solution was adjusted to 75° C. While the fermented solution is maintained at 75° C., an 86 wt. % aqueous solution of isopropanol at 20° C. was added thereto in an amount equal to 1.2 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

TESTING EXAMPLE 5

A xanthan gum-containing fermented solution prepared in the same manner as in Testing Example 1 was subjected to the same enzyme treatment as in Testing Example 1.

After completion of the enzyme treatment, the fermented solution was maintained at 55° C. While the fermented solution is maintained at 55° C., an 86 wt. % aqueous solution of isopropanol at 20° C. was added thereto in an amount equal to 1.5 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

TESTING EXAMPLE 6

A xanthan gum-containing fermented solution prepared in the same manner as in Testing Example 1 was subjected to a two-stage enzyme treatment in which the same two enzymes as in Testing Example 1 were used in the reverse order.

Specifically, while the fermented solution was being stirred, its initial pH was adjusted to 11 by the addition of a 20% aqueous solution of sodium hydroxide, followed by heat treatment at 55° C. for 90 minutes. Thereafter, while the fermented solution was maintained at 55° C., its pH was adjusted to 6.5 by the addition of a 10% aqueous solution of sulfuric acid. Then, lysozyme (Lysozyme Taiyo; manufactured by Taiyo Chemical Co., Ltd.) was added thereto in an amount of 3 ppm and a lysozyme treatment was carded out with stirring.

Next, while the fermented solution was maintained at 55° C., its pH was adjusted to 8.5 by the addition of a 20% aqueous solution of sodium hydroxide. On the other hand, an aqueous suspension containing an alkaline protease (Bioprase; manufactured by Nagase Biochemical Co., Ltd.) in an amount of 300 ppm based on the fermented solution was filtered through a 0.4 μm microfilter to remove the adsorbent. The resulting filtrate was added to the above pH-adjusted fermented solution and an alkaline protease treatment was carried out with stirring for 2 hours.

After completion of the enzyme treatment and after the pH of the fermented solution was adjusted to 7.0, xanthan gum was recovered from the fermented solution under the same conditions as in Testing Example 5, and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 1

A xanthan gum-containing fermented solution prepared in the same manner as in Testing Example 1 was subjected to the same enzyme treatment as in Testing Example 1.

After completion of the enzyme treatment, the fermented solution was adjusted to 45° C. While the fermented solution is maintained at 45° C., an 86 wt. % aqueous solution of isopropanol at 20° C. was added thereto in an amount equal to 1.5 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 2

A xanthan gum-containing fermented solution prepared in the same manner as in Testing Example 1 was subjected to the same enzyme treatment as in Testing Example 1.

After completion of the enzyme treatment, the fermented solution was adjusted to 20° C. While the fermented solution is maintained at 20° C., an 86 wt. % aqueous solution of isopropanol at 20° C. was added thereto in an amount equal to 2.0 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 3

A xanthan gum-containing fermented solution prepared in the same manner as in Testing Example 1 was subjected to the same enzyme treatment as in Testing Example 1.

After completion of the enzyme treatment, the fermented solution was adjusted to 20° C. While the fermented solution is maintained at 20° C., an 86 wt. % aqueous solution of isopropanol at 20° C. was added thereto in an amount equal to 1.5 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 4

A xanthan gum-containing fermented solution prepared in the same manner as in Testing Example 1 was subjected to the same enzyme treatment as in Testing Example 1.

After completion of the enzyme treatment, the fermented solution was adjusted to 20° C. While the fermented solution is maintained at 20° C., an 86 wt. % aqueous solution of isopropanol at 20° C. was added thereto in an amount equal to 1.2 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 5

A xanthan gum-containing fermented solution prepared in the same manner as in Testing Example 1 was subjected to the same enzyme treatment as in Testing Example 1.

After completion of the enzyme treatment, the fermented solution was adjusted to 88° C. While the fermented solution is maintained at 88° C., an 86 wt. % aqueous solution of isopropanol at 20° C. was added thereto in an amount equal to 1.3 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 6

A xanthan gum-containing fermented solution prepared in the same manner as in Testing Example 1 was subjected to the same enzyme treatment as in Testing Example 1.

After completion of the enzyme treatment, the fermented solution was maintained at 55° C. While the fermented solution is maintained at 55° C., an 86 wt. % aqueous solution of isopropanol at 20° C. was added thereto in an amount equal to 2.0 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 7

A xanthan gum-containing fermented solution prepared in the same manner as in Testing Example 1 was subjected to the same enzyme treatment as in Testing Example 1.

After completion of the enzyme treatment, the fermented solution was maintained at 55° C. While the fermented solution is maintained at 55° C., an 86 wt. % aqueous solution of isopropanol at 45° C. was added thereto in an amount equal to 2.5 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 8

A xanthan gum-containing fermented solution prepared in the same manner as in Testing Example 1 was subjected to the same enzyme treatment as in Testing Example 1.

After completion of the enzyme treatment, the fermented solution was maintained at 55° C. While the fermented solution is maintained at 55° C., an 86 wt. % aqueous solution of isopropanol at 20° C. was added thereto in an amount equal to 0.8 time the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 9

A xanthan gum-containing fermented solution prepared in the same manner as in Testing Example 1 was subjected to the same enzyme treatment as in Testing Example 1.

After completion of the enzyme treatment, the fermented solution was maintained at 55° C. While the fermented solution is maintained at 55° C., a 75 wt. % aqueous solution of isopropanol at 20° C. was added thereto in an amount equal to 1.5 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 10

A xanthan gum-containing fermented solution prepared in the same manner as in Testing Example 1 was subjected to the same enzyme treatment as in Testing Example 1.

After completion of the enzyme treatment, the fermented solution was maintained at 55° C. While the fermented solution is maintained at 55° C., a 60 wt. % aqueous solution of isopropanol at 20° C. was added thereto in an amount equal to 1.3 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

COMPARATIVE EXAMPLE 11

A xanthan gum-containing fermented solution prepared in the same manner as in Testing Example 1 was subjected to the same enzyme treatment as in Testing Example 1.

After completion of the enzyme treatment, the fermented solution was maintained at 55° C. While the fermented solution is maintained at 55° C., a 55 wt. % aqueous solution of isopropanol at 45° C. was added thereto in an amount equal to 1.5 times the weight of the fermented solution. Using the same mixing apparatus as in Testing Example 1, xanthan gum was precipitated and its state of precipitation was evaluated. Then, the precipitated xanthan gum was recovered and dried in a stream of air. The resulting xanthan gum was analyzed in the same manner as in Testing Example 1.

The results thus obtained are shown in Table 1. The analytical methods employed are as described in Testing Example 1.

TABLE 1

RESULTS OF TESTING EXAMPLES AND COMPARATIVE EXAMPLES

| | | | Solid xanthan gum | | 1 wt. % aqueous solution of xanthan gum | |
|---|---|---|---|---|---|---|
| | State of precip- itation | Amount of IPA used (kg) | Nitro- gen content (wt. %) | Ash content (wt. %) | Vis- cosity (cP) | Light trans- mit- tance (%) | Yel- low- ness Index |
| Testing Example 1 | o | 1,450 | 0.35 | 9.2 | 1,540 | 81 | 9.4 |
| Testing Example 2 | o | 1,450 | 0.35 | 9.2 | 1,530 | 82 | 9.3 |
| Testing Example 3 | o | 1,700 | 0.34 | 9.1 | 1,550 | 82 | 9.3 |
| Testing Example 4 | o | 1,550 | 0.32 | 9.0 | 1,590 | 83 | 9.2 |
| Testing Example 5 | o | 1,950 | 0.31 | 8.8 | 1,620 | 85 | 9.0 |
| Testing Example 6 | o | 1,950 | 0.31 | 8.9 | 1,600 | 84 | 9.1 |

TABLE 1-continued

RESULTS OF TESTING EXAMPLES AND COMPARATIVE EXAMPLES

| | | Solid xanthan gum | | | 1 wt. % aqueous solution of xanthan gum | | |
|---|---|---|---|---|---|---|---|
| | State of precipitation | Amount of IPA used (kg) | Nitrogen content (wt. %) | Ash content (wt. %) | Viscosity (cP) | Light transmittance (%) | Yellowness Index |
| Comparative Example 1 | o | 1,950 | 0.57 | 10.6 | 1,510 | 78 | 11.0 |
| Comparative Example 2 | o | 2,600 | 0.85 | 13.2 | 1,480 | 75 | 18.4 |
| Comparative Example 3 | Δ | 1,950 | 0.88 | 13.5 | 1,400 | 74 | 18.7 |
| Comparative Example 4 | x | 1,550 | — | — | — | — | — |
| Comparative Example 5 | o | 1,700 | 0.31 | 8.9 | 1,230 | 82 | 9.2 |
| Comparative Example 6 | o | 2,600 | 0.31 | 8.7 | 1,610 | 85 | 9.0 |
| Comparative Example 7 | o | 3,250 | 0.30 | 8.7 | 1,520 | 85 | 9.0 |
| Comparative Example 8 | x | 1,000 | — | — | — | — | — |
| Comparative Example 9 | Δ | 1,950 | 0.46 | 10.9 | 1,520 | 80 | 10.6 |
| Comparative Example 10 | x | 1,700 | — | — | — | — | — |
| Comparative Example 11 | x | 1,950 | — | — | — | — | — |

(Note)
o = Good
Δ = Fair
x = Poor

It can be seen from the foregoing testing examples and comparative examples that, according to the process of the present invention wherein a xanthan gum-containing fermented solution is heat-treated, subjected to a two-stage enzyme treatment with two types of bacteriolytic enzymes (i.e., an alkaline protease and lysozyme), fed to a rotary turbine while being maintained at an elevated temperature, and mixed with isopropanol (i.e., a hydrophilic organic solvent incapable of dissolving xanthan gum) to precipitate and recover xanthan gum in the form of a finely-divided fibrous product, the amount of isopropanol used can be reduced by about 20% as compared with that used in the conventionally known treatment at room temperature. Moreover, there can be obtained highly purified xanthan gum which is characterized in that a 1 wt. % aqueous solution of the recovered xanthan gum has a viscosity of greater than 1,000 cP [as measured with a Brookfield viscometer (30 rpm)] without detracting from the inherent viscosity of xanthan gum, a light transmittance of greater than 80%, and a yellowness index of less than 10, and the recovered xanthan gum has a nitrogen content of less than 0.5% by weight and an ash content of less than 10% by weight.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A process for the recovery and purification of xanthan gum from an aqueous fermentation broth containing dissolved xanthan gum and microbial cellular debris which comprises:

a) adjusting the pH of the broth to an initial pH of 9 to 12.5;

b) heating the solution from step a at a temperature of 45° to 70° C. for at least 30 minutes;

c) immediately after step b), adding an alkaline protease to the solution obtained from step b) in an amount of from 10 to 500 ppm and heating the solution at a temperature of 40° to 65° C. and a pH of 6 to 10 for at least 30 minutes; and then, d) adding lysozyme to the solution obtained from step c) in an amount of 0.5 to 100 ppm and heating the solution at a temperature of 25° to 60° C. and a pH of 5.5 to 8.0 for at least 30 minutes;

e) maintaining the broth obtained from step d) at a temperature of 50° to 80° C. for at least about 30 minutes; and then f) adding a hydrophilic organic non-solvent for xanthan gum to the broth obtained from step e) to precipitate the dissolved xanthan gum and recovering the precipitated xanthan gum from the broth.

2. A process for the recovery and purification of xanthan gum from an aqueous fermentation broth containing dissolved xanthan gum and microbial cellular debris which comprises:

a) adjusting, if necessary, the pH of the broth to an initial pH of 9 to 12.5;

b) heating the solution from step a) at a temperature of 45° to 70° C. for at least 30 minutes;

c) immediately after step b), adding lysozyme to the solution obtained from step b) in an mount of 0.5 to 100 ppm and heating the solution at a temperature of 25° to 60° C. and a pH of 5.5 to 8.0 for at least 30 minutes; and then, d) adding an alkaline protease to the solution obtained from step c) in an amount of 10 to 500 ppm and carrying out an alkaline protease treatment at a temperature of 40° to 65° C. and a pH of 6 to 10 for at least 30 minutes.

e) maintaining the broth obtained from step a) at a temperature of 50° to 80° C. for at least about 30 minutes; and then f) adding a hydrophilic organic non-solvent for xanthan gum to the broth obtained from step e) to precipitate the xanthan gum in the broth and recovering the xanthan gum therefrom.

3. The process of claim 1 or 2 wherein the hydrophilic organic non-solvent is isopropanol or an aqueous solution of isopropanol having an isopropanol concentration of not less than 80% by weight.

4. The process of claim 1 or 2 wherein in step f), the weight ratio of the broth to hydrophilic organic non-solvent ranges from 1:1.0 to 1:1.5.

5. The process of claim 1 or 2 wherein the heating step b) is carried out at a temperature in the range from about 50° C. to 60° C.

6. The process of claim 1 or 2 wherein the heating step b) is carried out at a pH in the range from about 9 to 12.5.

7. The process of claim 1 or 2 wherein step f) is carried out by forming a mixture of the broth from step e) and the non-solvent to produce a xanthan gum precipitate, feeding the mixture to a cutting device and cutting the precipitate in the mixture to produce a finely-divided xanthan gum, and separating and recovering the suspended finely-divided xanthan gum from the mixture.

8. The process of claim 1 or 2 wherein step c) is carried out at a temperature from about 50° to 60° C.

9. The process of claim 1 or 2 wherein step d) is carried out at a temperature from about 50° to 60° C.

10. The process of claim 2 wherein step d) is carried out at a temperature from about 50° to 60° C.

11. The process of claim 1 or 2 wherein step f) is carried out by feeding the broth from step e) and the non-solvent to a cutting device and rotary turbine to form a mixture thereof and form a precipitate of xanthan gum in the mixture, cutting the precipitate in the mixture with a shearing cutter to obtain a finely-divided fibrous xanthan gum and separating and recovering the suspended finely-divided fibrous xanthan gum from the mixture.

12. Xanthan gum obtained from the process of claim 1 or 2 having a nitrogen content of less than 0.5% by weight, an ash content of less than 10% by weight, and a light transmittance of greater than 80%, a yellowness index of less than 10, and a Brookfield viscosity of greater than 1,000 centipoise.

13. Xanthan gum obtained from the process of claim 7 having a nitrogen content of less than 0.5% by weight, an ash content of less than 10% by weight, and a light transmittance of greater than 80%, a yellowness index of less than 10, and a Brookfield viscosity of greater than 1,000 centipoise.

14. Xanthan gum obtained from the process of claim 11 having a nitrogen content of less than 0.5% by weight, an ash content of less than 10% by weight, and a light transmittance of greater than 80%, a yellowness index of less than 10, and a Brookfield viscosity of greater than 1,000 centipoise.

* * * * *